(12) United States Patent
Grover et al.

(10) Patent No.: US 12,178,588 B2
(45) Date of Patent: *Dec. 31, 2024

(54) METHOD FOR DETECTING AND LOCALIZING BRAIN SILENCES USING EEG

(71) Applicant: CARNEGIE MELLON UNIVERSITY, Pittsburgh, PA (US)

(72) Inventors: Pulkit Grover, Pittsburgh, PA (US); Alireza Chamanzar, Pittsburgh, PA (US); Marlene Behrmann Cohen, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/410,446

(22) Filed: Jan. 11, 2024

(65) Prior Publication Data
US 2024/0252096 A1    Aug. 1, 2024

Related U.S. Application Data

(63) Continuation of application No. 17/183,545, filed on Feb. 24, 2021, now Pat. No. 11,925,470.

(60) Provisional application No. 62/992,201, filed on Mar. 20, 2020.

(51) Int. Cl.
*A61B 5/00*  (2006.01)
*A61B 5/055*  (2006.01)
*A61B 5/372*  (2021.01)

(52) U.S. Cl.
CPC ............ *A61B 5/372* (2021.01); *A61B 5/0042* (2013.01); *A61B 5/055* (2013.01); *A61B 5/7264* (2013.01)

(58) Field of Classification Search
CPC ....... A61B 5/372; A61B 5/0042; A61B 5/055; A61B 5/7264; A61B 5/374; A61B 5/7246
See application file for complete search history.

(56) References Cited

U.S. PATENT DOCUMENTS 11,925,470 B2 *  3/2024  Grover ................... A61B 5/372

\* cited by examiner

*Primary Examiner* — Jeffrey G Hoekstra
*Assistant Examiner* — Gabriel Victor Popescu
(74) *Attorney, Agent, or Firm* — KDW Firm PLLC

(57) ABSTRACT

A novel method for using the widely-used electroencephalography (EEG) systems to detect and localize silences in the brain is disclosed. The method detects the absence of electrophysiological signals, or neural silences, using non-invasive scalp electroencephalography (EEG) signals. This method can also be used for reduced activity localization, activity level mapping throughout the brain, as well as mapping activity levels in different frequency bands. By accounting for the contributions of different sources to the power of the recorded signals and using a hemispheric baseline approach and a convex spectral clustering framework, the method permits rapid detection and localization of regions of silence in the brain using a relatively small amount of EEG data.

14 Claims, 3 Drawing Sheets

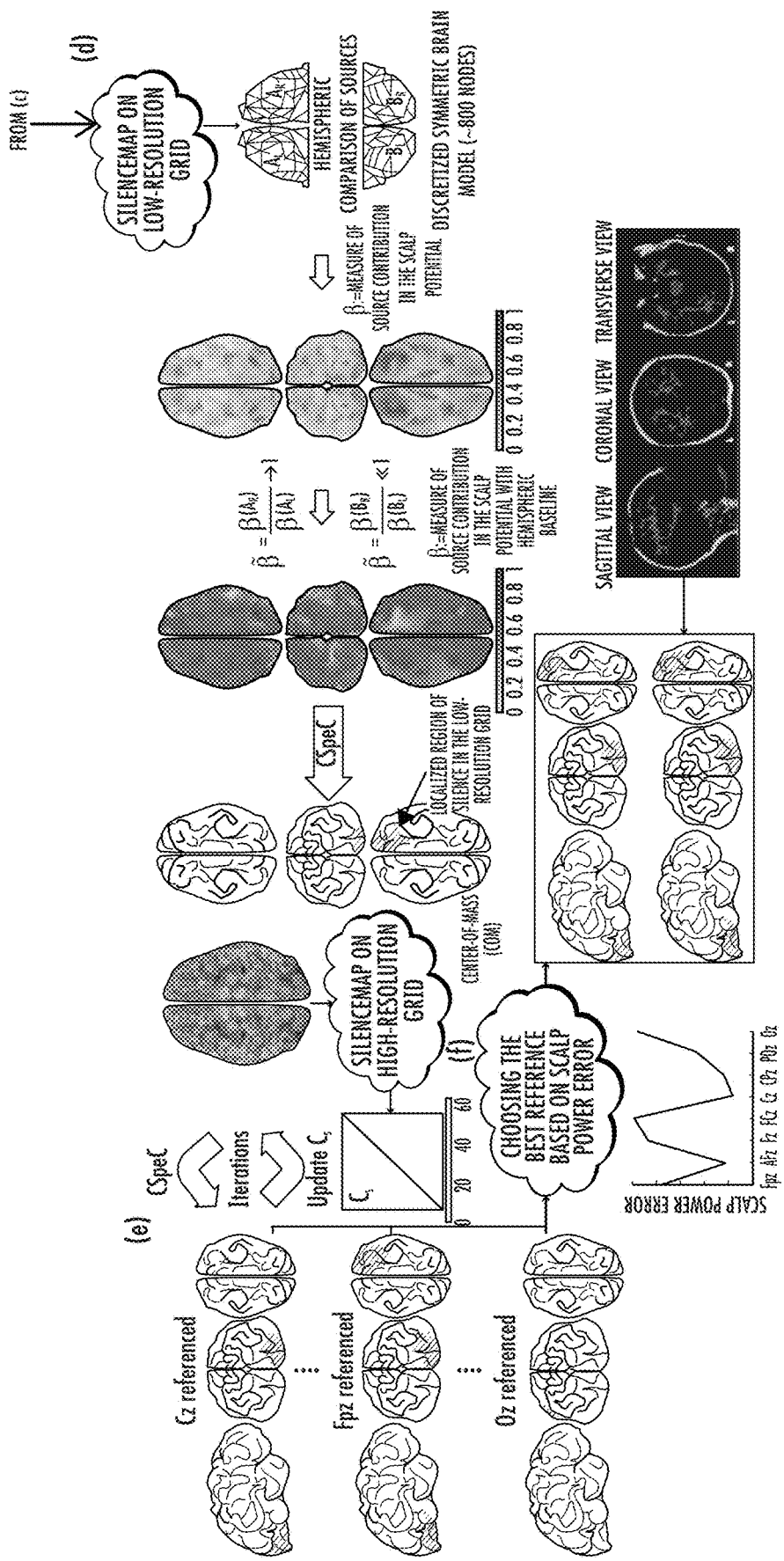
FIG. 1, CONT.

| | ASSUMPTION | EFFECT | POSSIBLE WAYS TO RELAX THESE ASSUMPTIONS |
|---|---|---|---|
| (ii) | SPATIO-TEMPORAL INDEPENDENCE OF ADDITIVE NOISE $\tilde{E}$ | IT AFFECTS THE NOISE VARIANCE ESTIMATION | USING MORE REALISTIC ASSUMPTIONS ON THE GENERAL SHAPE OF NOISE PSD (NONFLAT PSD), AND THE SPATIAL CORRELATION PROFILE (NON-DIAGONAL $C_z$), NOISE VARIANCE ESTIMATION CAN BE IMPROVED. |
| (iii) | SPATIAL EXPONENTIAL DECAY PROFILE FOR THE SOURCE COVARIANCE MATRIX $C_s$, WITH IDENTICAL VARIANCES ($\sigma_s^2$) FOR ALL NON-SILENT SOURCES | IT AFFECTS THE SOURCE COVARIANCE ESTIMATION IN SILENCEMAP (SEE EQUATION 30) | USING MORE REALISTIC AND DATA-DRIVEN ASSUMPTIONS ON THE SPATIAL CORRELATION PROFILE OF BRAIN SOURCES, AS WELL AS ESTIMATION OF NON-IDENTICAL SOURCE VARIANCES BASED ON BASELINE RECORDINGS OF SILENCES. |
| (vi) | CONTIGUITY OF SILENT SOURCES AS A SINGLE REGION OF SILENCE | IT AFFECTS THE DESIGN OF THE CSPEC FRAMEWORK PROPOSED IN SILENCEMAP (SEE EQUATIONS 32 AND 14) | WITH THE ASSUMPTION OF MULTIPLE REGIONS OF SILENCE, WITH DIFFERENT SIZES, USING METHODS SUCH AS THE EXTENSION OF CSpeC METHOD FOR MULTIPLE CLUSTERS IN A GRAPH CAN BE USED IN SILENCEMAP. |
| (vii) | SILENCE LIES IN ONLY ONE HEMISPHERE | BASED ON THIS ASSUMPTION, USE THE HEMISPHERIC BASELINE FOR SILENCE LOCALIZATION. | THIS ASSUMPTION CAN BE RELAXED IF WE HAVE A BASELINE RECORDING FOR THE REGIONS OF SILENCE (E.G., RECORDING OF THE BRAIN WITHOUT ANY SILENCE). |
| (vii) | HEMISPHERIC SYMMETRY OF SCALP POTENTIALS FOR REGIONS FAR FROM SILENCE | BASED ON THIS ASSUMPTION, USE HEMISPHERIC BASELINE AND SELECT A SUBSET OF SCALP ELECTRODES TO ESTIMATE THE SOURCE COVARIANCE MATRIX (SEE EQUATIONS 28 AND 29). | THIS ASSUMPTION CAN BE RELAXED IF WE HAVE A BASELINE RECORDING FOR THE REGIONS OF SILENCE (E.G., RECORDING OF THE BRAIN WITHOUT ANY SILENCE), AND USE A NON-IDENTICAL DISTRIBUTION MODEL FOR THE NON-SILENT SOURCE ACTIVITIES. |

FIG. 2

METHOD FOR DETECTING AND LOCALIZING BRAIN SILENCES USING EEG

RELATED APPLICATIONS

This application is a continuation of U.S. patent application Ser. No. 17/183,545, filed Feb. 24, 2021, which claims the benefit of U.S. Provisional Patent Application No. 62/992,201, filed Mar. 20, 2020, the contents of which are incorporated herein in their entirety.

GOVERNMENT INTEREST

This invention was made with U.S. government support under contract CNS1702694, awarded by the National Science Foundation. The U.S. government has certain rights in the invention.

BACKGROUND

Brain "silences" are sources in the brain without any electrophysiological activity. Parts of brain tissue with neural silences (i.e., with little or no neural activity) are referred to as "regions of silence". These regions contain ischemic, necrotic, or lesional tissue (e.g., after ischemic stroke, traumatic brain injuries (TBIs), and intracranial hematoma), resected tissue (e.g. after epilepsy surgery), or tumors in the brain. In addition. neural silences may occur associated with neurodegenerative disorders, for example, Alzheimer's disease, Huntington's disease, and posterior conical atrophy, although these are generally somewhat more diffuse than a circumscribed focal lesion. Dynamic regions of silence also arise in cortical spreading depolarizations (CSDs), which are slowly spreading waves of neural silences in the cerebral cortex after concussion, TBI, stroke, and some other neurological diseases.

Common imaging methods for detection of regions of silence, for example, magnetic resonance imaging (MRI), or computed tomography (CT), are not portable, not designed for continuous (or frequent) monitoring, are difficult to use in many emergency situations and may not be available at medical facilities in many locations. However, many medical scenarios can benefit from portable, frequent and/or continuous monitoring, e.g., detecting changes in tumor or lesion size and location, indicating expansion or shrinkage), and/or propagation of CSD in the brain.

On the other hand, non-invasive EEG is widely accessible in emergency situations and can even be deployed in the field with only a few limitations. It is easy and fast to setup, portable, and of lower relative cost compared with other imaging modalities. Additionally, unlike MRI, EEG can be recorded from patients with implanted metallic objects in their body, for example, pacemakers.

One ongoing challenge in the use of EEG is source localization, the process by which the location of the underlying neural activity is determined from the scalp EEG recordings. The challenge arises primarily from three issues: (i) the underdetermined nature of the problem (few sensors, many possible locations of sources); (ii) the spatial low-pass filtering effect of the distance and the layers separating the brain and the scalp; and (iii) noise, including exogenous noise, background brain activity, as well as artifacts, e.g., heart beats, eye movements, and jaw clenching. In source localization paradigms applied to neuroscience data, for example, in event-related potential paradigms, scalp EEG signals are aggregated over event-related trials to average out background brain activity and noise, permitting the extraction of the signal activity that is consistent across trials.

The localization of a region of silence poses additional challenges, of which the most important is how the background brain activity is treated. Typically, in source localization, the background brain activity is grouped with noise and ignored. Estimating where background activity is present is of direct interest in silence localization where the goal is to separate normal brain activity (including background activity) from abnormal silences. Because source localization ignores this distinction, classical source localization techniques, e.g., multiple signal classification (MUSIC), minimum norm estimation (MNE), and standardized low-resolution brain electromagnetic tomography (sLORETA), even after appropriate modifications, fail to localize silences in the brain.

Therefore, it would be desirable to provide a method of using EEG data to localize sources that is capable of separating background brain activity from noise, and to identify regions of silence in the brain, thereby providing a rapid and cost-effective tool to uncover details of neural function and dysfunction.

SUMMARY

Disclosed herein is a method for using widely-used electroencephalography (EEG) systems to detect and localize silences in the brain. The method detects the absence of electrophysiological signals, or neural silences, using non-invasive electroencephalography (EEG) signals. By accounting for the contributions of different sources to the power of the recorded signals, and using a hemispheric baseline approach and a convex spectral clustering framework, the method permits rapid detection and localization of a single region or multiple regions of silence in the brain using a relatively small amount of EEG data (on the order of a few minutes). The method substantially outperforms existing source localization algorithms in estimating the center-of-mass of the silence. The method provides an accessible way to perform early detection of abnormality, and continuous monitoring of altered physiological properties of human cortical function. This method can also be used for reduced activity localization, activity level mapping throughout the brain, as well as mapping activity levels in different frequency bands.

The method localizes regions of silence in two steps: The first step finds a contiguous region of silence (or multiple regions of silence) in a low-resolution source grid, as shown in FIG. 1($d$), with the assumption that, at this resolution, the sources are uncorrelated across space. The second step of the method adopts the localized regions of silence in the low-resolution source grid as an initial estimate of the location of the regions of silence in a high-resolution grid, as shown in FIG. 1($e$). Then, through iterations, each region of silence is localized based on an estimated source covariance matrix $C_s$, until the center-of-mass (COM) of the localized region of silence converges.

In the low-resolution grid, given that the sources are sufficiently separated, a reasonable approximation is to assume they have independent activity. A measure for the contribution of brain sources to the recorded scalp signals is defined as $\beta$. The larger the $\beta$, the greater the contribution of the brain source to the scalp potentials. However, $\beta$ is not a perfect measure of the contribution because it is defined based on an identical distribution assumption on the non-silent sources, which does not hold in the real world.

Therefore, using β does not reveal the silent sources, that is, the smallest values of β, shown as the yellow regions in FIG. 1(d), may not be located at the region of silence. But, looking closely at the values of β in the inferior surface of the brain reveals a large hemispheric color difference at the region of silences (right occipito-temporal lobe). This motivates the use of a hemispheric baseline in which, instead of using β, $\tilde{\beta}$ is defined as the ratio of β values of the mirrored sources from the opposite hemisphere of the brain (e.g., for source pair $(A_L, A_R)$, which are remote from the region of silence(s), $\tilde{\beta}$ is close to 1, shown as the red-colored areas, while for $(B_L, B_R)$, where $B_R$ is located in the region of silences (see FIG. 1(d)), this ratio is close to zero (i.e., yellow-colored sources)). A contiguous region of silence is localized based on a convex spectral clustering (CSpeC) framework. The algorithm estimates the contiguous region of silence by determining the contribution of each source (dipole) in recorded signals and detects the sources with a reduced contribution as silences in the brain, using an iterative method based on the CSpeC framework.

To avoid averaging out the background brain activity, the method estimates the contribution of each source to the recorded EEG across all electrodes. This contribution is measured in an average power sense, instead of the mean, thereby retaining the contributions of the background brain activity. The method estimates these contributions and uses tools that quantify certain assumptions on the region of silence (contiguity and small size of the region of silence) to localize the region. Because of this, another difference arises: silence localization can use a larger number of time points as opposed to typical source localization, thereby boosting the signal-to-noise ratio (SNR) as compared to source localization techniques, which typically rely on only a few tens of event-related trials to average over and extract the source activity that is consistent across trials.

Further, the method addresses two additional difficulties: lack of statistical models of background brain activity, and the choice of the reference electrode. The first is dealt with either by including baseline recordings or utilizing a hemispheric baseline, i.e., an approximate equality in power measured at electrodes placed symmetrically with respect to the longitudinal fissure, as shown in FIG. 1(b). While the hemispheric baseline provides fairly accurate reconstructions, it is only an approximation, and an actual baseline will further improve the accuracy of the method. The second difficulty is related. To retain this approximate hemispheric symmetry in power, it is best to utilize a reference electrode on top of the longitudinal fissure, as shown in FIG. 1(a). Using these advances, the method is able to localize the region of silence in the brain using a relatively small amount of data.

BRIEF DESCRIPTION OF THE DRAWINGS

FIG. 2 is a table showing assumptions used in the method and their effects on the outcome.

DETAILED DESCRIPTION

Figure 1:
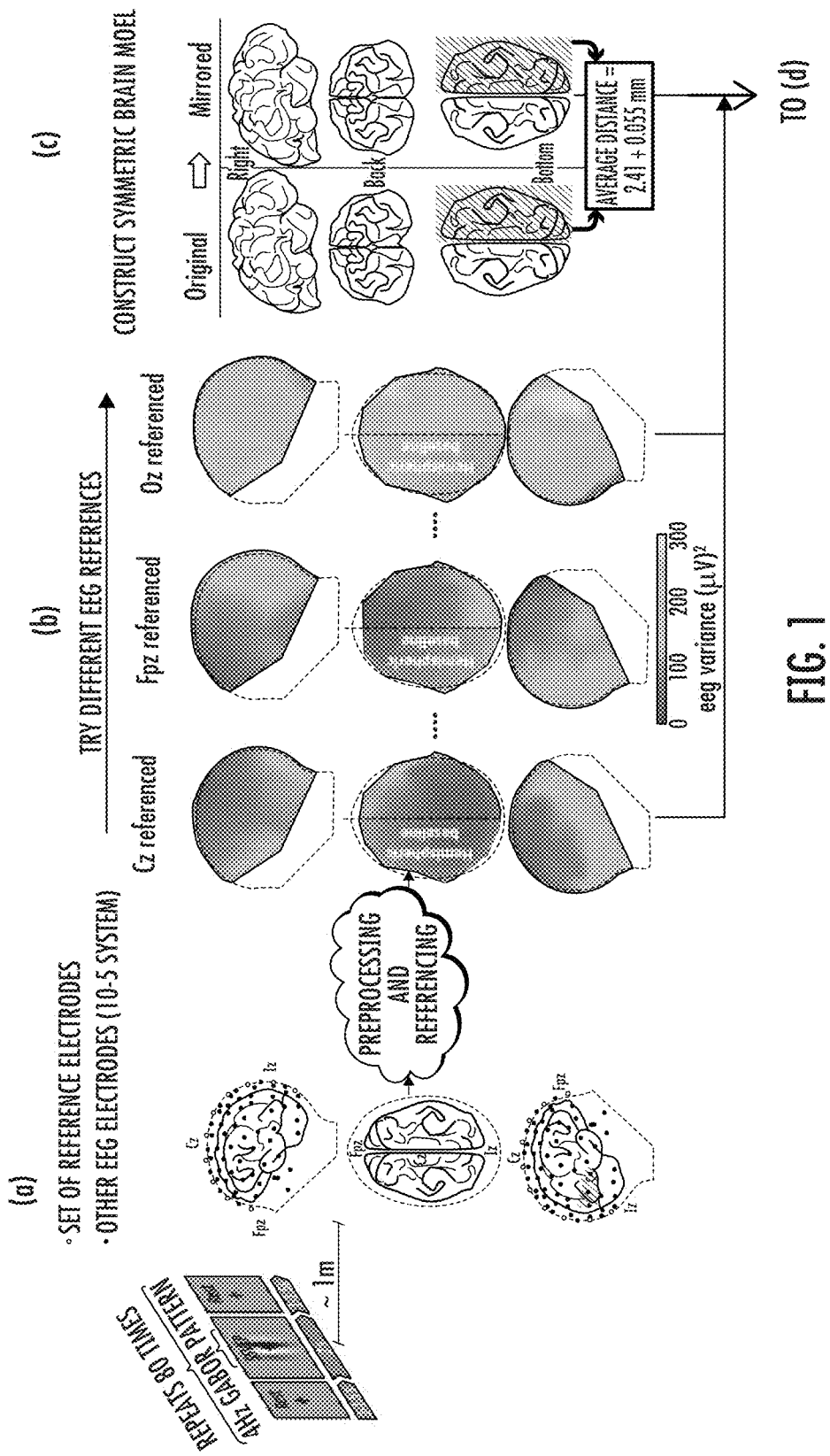
FIGS. 1(a)-1(e) show a graphical representation of the steps of the method.

Disclosed herein is a novel method, including an algorithm, that localizes contiguous regions of silence in the brain based on non-invasive scalp EEG signals. The novel technical ideas introduced here are related to ensuring that background brain activity is separated from silences, using a hemispheric baseline, careful referencing, and utilization of a convex optimization framework for clustering. The method of the invention substantially outperforms appropriately modified state-of-the-art source localization algorithms, such as MNE, MUSIC and sLORETA, and reduces the distance error (ΔCOM).

Herein, non-bold letters and symbols (e.g., α, γ and θ) are used to denote scalars; lowercase bold letters and symbols (e.g., α, γ and θ) denote vectors; uppercase bold letters and symbols (e.g., A, E and Δ) denote matrices, and script fonts (e.g., $\mathcal{S}$) denote sets. Also, as used herein, the term "region of silence" refers to a singular region of silence or plural regions of silence.

Following the standard approach in source localization problems, the linear approximation of the well-known Poisson's equation is used to write a linear equation which relates the neural electrical activities in the brain to the resulting scalp potentials. This linear equation is called the "forward model". In this model, each group of neurons are modeled by a current source or dipole, which is assumed to be oriented normal to the cortical surface.

The linear forward model can be written as:

$$X_{n \times T} = A_{n \times p} S_{p \times T} + E_{n \times T} \tag{1}$$

where:
A is a forward matrix indicating the location of the sources in the brain;
X is the matrix of measurements, with each row representing the signal of one electrode, with reference at infinity, across time;
S is the matrix of source signals;
E is the measurement noise;
T is the number of time points;
p is the number of sources, and
n is the number of scalp sensors.

Note that the forward matrix A may be obtained from an actual MRI of the brain. In the absence of an actual MRI scan of the brain, a template head model may be used, which can come from averaged MRI scans from a plurality of individuals or an MRI scan of a single reference individual.

In practice, the matrix X is unavailable because the reference at infinity cannot be recorded. Only a differential recording of scalp potentials is possible. If an (n−1)×n matrix M is defined with the last column to be all −1 and wherein the first (n−1) columns compose an identity matrix, the differential scalp signals, with the last electrode's signal as the reference, can be written as follows:

$$Y_{(n-1) \times T} = M_{(n-1) \times n} X_{n \times T} = M_{(n-1) \times n} A_{n \times p} S_{p \times T} + M_{(n-1) \times n} E_{n \times T} \tag{2}$$

where:
Y is the matrix of differential signals of the scalp; and
M is a matrix of linear transformation, which transforms the scalp signals with reference at infinity in the matrix X, to be differential signals in Y. Eq. (2) can be rewritten as follows:

$$Y_{(n-1) \times T} = \tilde{A}_{(n-1) \times p} S_{p \times T} + \tilde{E}_{(n-1) \times T} \tag{3}$$

where:

Ã=MA; and

Ẽ=ME.

The objective is then: given M, Y and A, estimate the region of silence in S.

For this objective, two different scenarios are considered: (1) there are no baseline recordings for the region of silence (i.e., no scalp EEG recording is available where there is no region of silence); and (2) with hemispheric baseline recording (i.e., the recording of the hemisphere of the brain, left or right, which does not have any region of silence, is considered as a baseline for the silence localization task). Note that the location of the baseline hemisphere (left or right) is not assumed to be known a priori. Rather, locating the region of silence is the goal of this approach.

The following assumptions are made: (i) A and M are known, and Y has been recorded; (ii) Ẽ is additive, wide-sense stationary (WSS) zero-mean noise, which is differentially recorded and whose elements are assumed to be independent across space. Thus, at each time point, the covariance matrix is $C_z$ given by:

$$C_{z_{ij}} = \sigma_{z_i}^2, \text{ for all } i = j \quad (4)$$

$$C_{z_{ij}} = 0, \text{ for all } i \neq j$$

where:

$\sigma_{z_i}^2$ is the noise invariance at electrode i, and is assumed to be known;

(iii) k rows of S correspond to the region of silence, which are rows of all zeros. The correlations of source activities reduces as the spatial distance between the sources increases. A spatial exponential decay profile is assumed for the source covariance matrix $C_s$, with identical variances for all non-silent sources ($\sigma_{z_i}^2$):

$$C_{s_{ij}} = \sigma_s^2 e^{-\gamma \|f_i - f_j\|_2^2}, \text{ for all } i, j \notin \mathcal{S} \quad (5)$$

$$C_{s_{ij}} = 0, \text{ for all } i, j \in \mathcal{S}$$

where:

$f_i$ is the 3D location of source i in the brain;

$\gamma$ is the exponential decay coefficient; and $\mathcal{S}$ is the set of indices of silent sources ( $\mathcal{S} := \{i | S_{it} = 0$ for all $t \in \{1, 2, \ldots, T\}\}$).

It is assumed that the elements of S have zero mean and follow a WSS process; (iv) M is a (n−1)×n matrix where the last column is $-\mathbb{1}_{(n-1) \times 1}$ and the first n−1 columns form an identity matrix ($I_{(n-1) \times (n-1)}$); (v) it is assumed that p−k≫k, where p−k is the number of active (i.e., non-silent) sources and k is the number of silent sources; (vi) silent sources are contiguous. Contiguity is defined based on a z-nearest neighbor graph, where the nodes are the brain sources (i.e., vertices in the discretized brain model). In this z-nearest neighbor graph, two nodes are connected with an edge, if either or both of these nodes is among the z-nearest neighbors of the other node, where z is a known parameter. A contiguous region is defined as any connected subgraph of the defined nearest neighbor graph (between each two nodes in the contiguous region, there is at least one connecting path). This definition can be extended to multiple connected subgraphs (multiple regions of silence). However, the location of these regions are not assumed to be known.

In the absence of baseline recordings, estimating the region of silence proves difficult. To exploit prior knowledge about neural activity, the symmetry of the power of neural activity in the two hemispheres of a healthy brain is used. As an additional simplification, it is assumed that even when there is a region (or multiple regions) of silence, if the electrode is located far away from the region of silence, then the symmetry still holds. For example, if the silence is in the occipital region, then the power of the signal at the electrodes in the frontal region (after subtracting noise power) is assumed to be symmetric in the two hemispheres, that is, mirror images along the longitudinal fissure. This is only an approximation because: (a) the brain activity is not completely symmetric; and (b) a silent source affects the signal everywhere, even far from the silent source. Nevertheless, this assumption enables more accurate inferences about the location of the silence region in real data, with a baseline, as compared to an absence of a baseline recording. The simplification assumptions in this section are summarized in the table in FIG. 2, where the effect of each assumption, along with possible ways to relax them are shown.

The details of the two-step algorithm will now be provided, first in the situation wherein a baseline is unavailable and then with a hemispheric baseline.

If no baseline recording is available, the two-step silence localization algorithm is as follows:

Step 1: Low-resolution and uncorrelated sources: For the iterative method in the second step, an initial estimate of the region of silence is needed to select the electrodes whose powers are affected the least by the region of silence. The cortex is coarsely discretized to create a low-resolution source grid, with sources that are located far enough from each other such that the elements of S can be assumed to be uncorrelated across space:

$$c_{s_{ij}} = \sigma_S^2 \text{ for all } i = j \text{ \& } i, j \notin \mathcal{S} \quad (6)$$

$$c_{s_{ij}} = 0 \text{ for all } i \neq j \text{ or } i, j \in \mathcal{S}$$

Under this assumption of uncorrelatedness and identical distribution of brain sources in this low-resolution grid, a contiguous region of silence can be located through the following steps:

(i) Cross-correlation: Eq. (3) can be written in the form of linear combination of columns of matrix Ã as:

$$y_t = \sum_{i=1}^{p} \tilde{a}_i s_{it} + \tilde{\varepsilon}_t, \text{ for } t = \{1, 2, \ldots, T\} \quad (7)$$

where:

$s_{it}$ is the $i^{th}$ element of the $t^{th}$ column in S;

$Y = [y_1, \ldots y_T] \in \mathbb{R}^{(n-1) \times T}$;

$S = [s_1, \ldots, s_T] \in \mathbb{R}^{p \times T}$;

$\tilde{A} = [\tilde{\alpha}_1, \ldots, \tilde{\alpha}_p] \in \mathbb{R}^{(n-1) \times p}$; and $\tilde{E} = [\tilde{\varepsilon}_1, \ldots, \tilde{\varepsilon}_T] \in \mathbb{R}^{(n-1) \times T}$ Based on Eq. (7), each column vector of differential signals (i.e., $y_t$), is a weighted linear combination of columns of matrix Ã, with weights equal to the corresponding source values. However, in the presence of silences, the columns of Ã corresponding to the silent sources do not contribute to this linear combination. Therefore, we calculate the cross-correlation coefficient $\mu_{qt}$, which is a measure of the contribution of the $q^{th}$ brain source to the measurement vector $y_t$ (across all electrodes) at the $t^{th}$ time-instant, defined as follows:

$$\mu_{qt} = \tilde{a}_q^T y_t = \sum_{i=1}^{p} \tilde{a}_q^T \tilde{a}_i s_{it} + \tilde{a}_q^T \tilde{\varepsilon}_t \quad (8)$$

$$\text{for all } q = \{1, 2, \ldots, p\}, t = \{1, 2, \ldots, T\}$$

This measure is imperfect because the columns of the $\tilde{A}$ matrix are not orthogonal. The goal here is to attempt to quantify relative contributions of all sources to the recorded signals and to use that to arrive at a decision on which sources are silent because their contribution is zero.

(ii) Estimation of the Variance of $\mu_{qt}$: In this step, the variances of the correlation coefficients calculated in step (i) are estimated. Based on Eq. (8):

$$\text{Var}(\mu_{qt}) = \text{Var}\left(\sum_{i=1}^{p} \tilde{a}_q^T \tilde{a}_i s_{it} + \tilde{a}_q^T \tilde{\varepsilon}_t\right) \quad (9)$$

$$(a) \text{ Var} = \left(\sum_{i=1}^{p} \tilde{a}_q^T \tilde{a}_i s_{it}\right) + \text{Var}(\tilde{a}_q^T \tilde{\varepsilon}_t)$$

$$(b) \sum_{i=1}^{p} \text{Var}(\tilde{a}_q^T \tilde{a}_i s_{it}) + \text{Var}(\tilde{a}_q^T \tilde{\varepsilon}_t)$$

$$(c) \sum_{i=1}^{p} (\tilde{a}_q^T \tilde{a}_i)^2 \sigma_s^2 + \tilde{a}_q^T C_z \tilde{a}_q, i \notin \mathcal{S}$$

where:
$\mathcal{S}$ is the indices of silent sources.

In Eq. (9), the equality (a) holds because of independence of noise and sources, and the assumption that they have zero mean, equality (b) holds because the elements of $\mathcal{S}$ (i.e., the $s_{it}$'s) are assumed to be uncorrelated and have zero mean in the low-resolution grid, and equality (c) holds because the $S_{it}$'s are assumed to be identically distributed. It is important to note that $\sigma_s^2$ in Eq. (9) is a function of source grid discretization and it does not have the same value in the low-resolution and high-resolution grids. The variance of $\mu_{qt}$ is estimated using its power spectral density.

Based on Eq. (9), the variance of $\mu_{qt}$, excluding the noise variance, can be written as follows:

$$\widetilde{Var}(\mu_{qt}) = \text{Var}(\mu_{qt}) - \tilde{a}_q^T C_z \tilde{a}_q = \sum_{i=1}^{p} (\tilde{a}_q^T \tilde{a}_i)^2 \sigma_s^2, i \notin \mathcal{S} \quad (10)$$

where:
$\widetilde{Var}(\mu_{qt})$ is the variance of $\mu_{qt}$ without the measurement noise term, which is a function of the size and location of the region of silence through the indices in $\mathcal{S}$.

However, this variance term, as is, cannot be used to detect the silent sources, because some sources may be deep, and/or oriented in a way that they have weaker representation in the recorded signal $y_i$, and consequently have smaller $\text{Var}(\mu_{qt})$ and $\widetilde{Var}(\mu_{qt})$.

(iii) Source Contribution Measure ($\beta$): To be able to detect the silent sources and distinguish them from sources which inherently have different values of $\widetilde{Var}(\mu_{qt})$, The variance term for each source must be normalized by its maximum possible value (i.e., when there is no silent source, $$\widetilde{Var}_{max}(\mu_{qt}) = \sum_{i=1}^{p} (\tilde{a}_q^T \tilde{a}_i)^2 \sigma_s^2):$$

$$\overline{\text{Var}}(\mu_{qt}) = \frac{\widetilde{Var}(\mu_{qt})}{\widetilde{Var}^{max}(\mu_{qt})} = \frac{\widetilde{Var}(\mu_{qt})}{\sum_{i=1}^{p}(\tilde{a}_q^T \tilde{a}_i)^2 \sigma_s^2} \quad (11)$$

where:
$\overline{\text{Var}}(\mu_{qt})$ is the normalized variance of $\mu_{qt}$, without noise, and it takes values between 0 (all sources silent) and 1 (no silent source).

Note that it does not only depend on whether $q \in \mathcal{S}$, where $\mathcal{S}$ is the set of indices of silent sources. In general, this normalization requires estimation of source variance $\sigma_s^2$, but under the assumption that sources have identical distribution, they all have identical variances. Therefore, $\sigma_s^2$ in the denominator of Eq. (11) is the same for all sources. Both sides of Eq. (11) are multiplied by $\sigma_s^2$ to obtain:

$$\sigma_s^2 \overline{\text{Var}}(\mu_{qt}) = \frac{\widetilde{Var}(\mu_{qt})}{\sum_{i=1}^{p}(\tilde{a}_q^T \tilde{a}_i)^2} = \frac{\widetilde{Var}(\mu_{qt}) - \tilde{a}_q^T C_z \tilde{a}_q}{\sum_{i=1}^{p}(\tilde{a}_q^T \tilde{a}_i)^2} \quad (12)$$

Therefore:

$$\beta_q := \sigma_s^2 \overline{\text{Var}}(\mu_{qt}) = \frac{\text{Var}(\mu_{qt}) - \tilde{a}_q^T C_z \tilde{a}_q}{\sum_{i=1}^{p}(\tilde{a}_q^T \tilde{a}_i)^2} \approx \frac{\widetilde{Var}(\mu_{qt}) - \tilde{a}_q^T \widehat{C}_z \tilde{a}_q}{\sum_{i=1}^{p}(\tilde{a}_q^T \tilde{a}_i)^2} \quad (13)$$

where:
$\beta_q$ is the contribution of the $q^{th}$ source in the differential scalp signals in Y, which takes values between zero (all sources silent) and $\sigma_s^2$ (no silent sources).

In Eq. (13), $\widetilde{Var}(\mu_{qt})$ is an estimate of variance of $\mu_{qt}$, and $\widehat{C}_z$ Is an estimate of the noise covariance matrix.

(iv) Localization of silent sources in the low-resolution grid: In this step, the silent sources are found based on the $\beta_q$ values defined in the previous step, through a convex spectral clustering (CSpeC) framework as follows:

$$g*(\lambda, k) = \underset{g}{\text{argmin}} \ \beta^T(1-g) + \lambda(1-g)^T L(1-g), \quad (14)$$

$$\text{s.t. } g_i \in [0, 1], \text{ for all } i \in \{1, 2, \ldots, p\}, \|g\|_1 \leq p - k$$

where:
$\beta^T = [\beta_1, \ldots, \beta_T]$ is the vector of source contribution measures;
$g = [g_1, \ldots, g_p]^T$ is a relaxed indicator vector with values between zero (for silent sources) and one (for active sources);
k is the number of silent sources (i.e., the size of the region of silence)
$\lambda$ is a regularization parameter; and
L is a graph Laplacian matrix (defined in Eq. (19) below).
Based on the linear term in the cost function of Eq. (14), the optimizer finds the solution $g*$ that (ideally) has small values for the silent sources, and large values for the non-silent sources. The $\ell 1$ norm convex constraint controls the size of region of silence in the solution. To make the localized region of silence contiguous, the sources which are located far from each other must be penalized. This is done using the quadratic term in the cost function in Eq. (14) and through a graph spectral clustering approach, namely, relaxed RatioCut partitioning. A z-nearest neighbor undirected graph with the nodes to be the locations of the brain sources (i.e., vertices in the discretized brain model) is defined, and a weight matrix W is defined as follows:

$$w_{ij} = e^{\frac{\|f_i - f_j\|_2^2}{2\theta^2}}$$

for all i∈ z nearest neighbor of j OR j∈ z nearest neighbor of i $w_{ij}=0$ for all i∉z nearest neighbor of j OR j∉ z nearest neighbor of i  (15)

where the link weight is zero (no link) between nodes i and j, if node i is not among the z-nearest neighbors of j, and node j is not among the z-nearest neighbors of i.

In Eq. (15), z is chosen to be equal to the number of silent sources (i.e., z=k) and θ is an exponential decay constant, which normalizes the distances of sources from each other in a discretized brain model. Their variance is as follows:

$$\theta^2 = \text{Var}(\|f_i - f_j\|_2) \approx \frac{1}{N-1} \sum_{i=1}^{p} \sum_{j=i+1}^{p} (\|f_i - f_j\|_2 - \overline{\delta f})^2 \quad (16)$$

where:

$$N = \frac{p(p-1)}{2}$$

is the total number of inter-source distances; and $\overline{\delta f}$ is an estimated average of the inter-source distances, given by:

$$\overline{\delta f} = \frac{1}{N-1} \sum_{i=1}^{p} \sum_{j=i+1}^{p} \|f_i - f_j\|_2 \quad (17)$$

The degree matrix of the graph D is given by:

$$D = \left\{ [d_{ij}] \mid d_{ij} = \sum_{l=1}^{p} w_{il}, \text{ for all } i = j, \text{ and} \right\} \quad (18)$$

$$d_{ij} = 0, \text{ for all } i \neq j$$

Using the degree and weight matrices defined in Eq. (15) and Eq. (18), the graph Laplacian matrix L in Eq. (14), is defined as follows:

$$L = D - W \quad (19)$$

Based on one of the properties of the graph Laplacian matrix, the quadratic term in the objective function of Eq. (14) can be written as follows:

$$(1 - g)^T L (1 - g) = \frac{1}{2} \sum_{i,j=1}^{p} w_{ij}(g_i - g_j)^2 \quad (20)$$

where $g \in \mathbb{R}^p$.

This quadratic term promotes the contiguity in the localized region of silence, for example, an isolated node in the region of silence, which is surrounded by a number of active sources in the nearest neighbor graph, and which causes a large value in the quadratic term in Eq. (20), because $w_{ij}$ has large value due to the contiguity, and the difference $(g_i - g_j)$ has large value, since it is evaluated between pairs of silent (small $g_i$)-active (large $g_j$) sources.

For a given k, the regularization parameter λ in Eq. (14), is found through a grid-search and the optimal value (λ*) is found as the one which minimizes the total normalized error of source contribution and the contiguity term as follows:

$$\lambda_*(k) = \underset{\lambda}{\text{argmin}} \frac{\left(\beta^T (1 - g * (\lambda, k))\right)^2}{\underset{\lambda_1}{\max} \left(\beta^T (1 - g * (\lambda, k))\right)^2} + \quad (21)$$

$$\frac{\left((1 - g^*(\lambda, k))^T L (1 - g * (\lambda, k))\right)^2}{\underset{\lambda_2}{\max} \left((1 - g * (\lambda, k))^T L (1 - g * (\lambda, k))\right)^2}$$

In addition, the size of region of silence (i.e., k) is estimated through a grid-search as follows:

$$\hat{k} = \underset{k}{\text{argmin}} \sum_{i=1}^{n-1} \left\| \left(\tilde{A} C_S(k) \tilde{A}^T\right)_{ii} + \hat{\sigma}_{z_i}^2 - \widetilde{Var}(y_i) \right\|_2^2 \quad (22)$$

where:
(•)$_{ii}$ indicates the element of a matrix at the intersection of the $i^{th}$ row and the $i^{th}$ column;

$\widetilde{Var}(y_i)$ is the estimated variance of the $i^{th}$ differential signal in Y; and $\hat{\sigma}_{z_i}^2$, is the estimated noise variance at the $i^{th}$ electrode location.

In Eq. (22), $C_s(k)$ is the source covariance matrix, when there are k silent sources in the brain. The estimate $\hat{k}$ minimizes the cost function in Eq. (22), which is the squared error of difference between the powers of scalp differential signals, resulting from the region of silence with size k, and the estimated scalp powers based on the recorded data, with the measurement noise power removed. Under the assumption of identical distribution of sources, and lack of spatial correlation in the low-resolution source grid, and based on Eq. (6), Eq. (26) can be re-written as follows:

$$\hat{k} = \underset{k}{\text{argmin}} \sum_{i=1}^{n-1} \left\| \sum_{j=1, j \notin S}^{p} \tilde{a}_{ij}^2 \sigma_s^2 + \hat{\sigma}_{z_i}^2 - \widetilde{Var}(y_i) \right\|_2^2 = \quad (23)$$

-continued $$\underset{k}{\operatorname{argmin}} \sum_{i=1}^{n-1} \left\| \frac{\sum_{j=1, j \notin S}^{p} \tilde{a}_{ij}^2}{\max_{l} \sum_{j=1, j \notin S}^{p} \tilde{a}_{lj}^2} - \frac{\widehat{Var}(y_i) - \hat{\sigma}_{z_i}^2}{\max_{m} \widehat{Var}(y_m) - \hat{\sigma}_{z_m}^2} \right\|_2^2$$

where:
$\tilde{a}_{ij}$ is the element of matrix $\tilde{A}$ at the intersection of the $i^{th}$ row and the $j^{th}$ column; and
$S$ is the set of indices of k silent sources (i.e., indices of sources corresponding to the k smallest values in $g^*(\lambda^*, k)$, which is the solution to Eq. (14).

The second equality in Eq. (23) normalizes the power of electrode i using the maximum power of scalp signals for each i. This step eliminates the need to estimate $\sigma_s$ in the low-resolution.

Finally, the region of silence is estimated as the sources corresponding to the $\hat{k}$ smallest values in $g^*(\lambda^*, \hat{k})$. The 3D coordinates of the center-of-mass (COM) of the estimated contiguous region of silence in the low-resolution grid ($f_{COM}^{low}$), is used as an initial guess for the silence localization in the high-resolution grid, as explained in the next step.

Step 2: Iterative Algorithm Based on a High-Resolution Grid and Correlated Sources: In this step, a high-resolution source grid is used, where the sources are no longer uncorrelated. The source covariance matrix $C_s$ is estimated based on the spatial exponential decay assumption in Eq. (5). In each iteration, based on the estimated source covariance matrix, the region of silence is localized using a CSpeC framework.

(i) Initialization: In this step, the source variance $\sigma_s^2$ and the exponential decay coefficient in the source covariance matrix $\gamma$, and the set of indices of silent sources $S$ are initialized as follows:

$$\gamma^{(0)} = 1, \sigma_s^{2(0)} = 1 \qquad (24)$$

$$S^0 = \{i | \|f_i - f_{COM}^{low}\|_2^2 \le \|f_j - f_{COM}^{low}\|_2^2\}, \text{ for all } j = 1, 2, \ldots, p$$

where:
$S^0$ is the index of the nearest source in the high-resolution grid to the COM of the localized region of silence in the low-resolution grid $f_{COM}^{low}$.

For r=1, 2, . . . , R, the following steps are repeated until either the maximum number of iterations (R) is reached, or the COM of the estimated region of silence $f_{COM}^{high^{(r)}}$ has converged, where $f_{COM}^{high^{(0)}}$ is the location of the source with index $S^0$ in the high-resolution grid. The convergence criterion is defined as below:

$$\left\| f_{i,COM}^{high^j} - f_{i,COM}^{high^{(j-1)}} \right\|_2 \le \delta, \text{ for } j \in \{r-1, r\}, r \ge 2 \qquad (25)$$

where:
δ is a convergence parameter for COM displacement through iterations; and
$f_{COM}^{high} \in \mathbb{R}^{3 \times 1}$.

(ii) Estimation of $\sigma_s^2$ and γ: In this step, the source variance $\sigma_s^2$, and the exponential decay coefficient of source covariance matrix γ are estimated, based on their values in the previous iteration and the indices of silent sources in $S^{r-1}$. $C_s^{full}$ is defined as the source covariance matrix when there are no silent sources in the brain, and it is used to measure the effect of the region of silence on the power of each electrode. The source covariance matrix in the previous iteration (r−1) is calculated as follows:

$$C_s^{full(r-1)} = \left\{ [c_{s_{ij}}] \middle| c_{s_{ij}} = \sigma_s^{2(r-1)} e^{-\gamma^{(r-1)} \|f_i - f_j\|^2} \right\}, \qquad (26)$$

for all $i, j \notin S^{(r-1)}$ and $c_{s_{ij}} = 0$ if $i$ or $j \in S^{(r-1)}$ and $C_s^{full}$ is given by:

$$C_s^{full(r-1)} = \left\{ [c_{s_{ij}}] \middle| c_{s_{ij}} = \sigma_s^{2(r-1)} e^{-\gamma^{(r-1)} \|f_i - f_j\|^2} \right\}, \qquad (27)$$

for all $i, j = 1, 2, \ldots, p$ where there is no zero row and/or column (i.e., there is no silence).

To be able to estimate $\sigma_s^2$ and γ based on the differentially recorded signals in Y, the electrodes which are the least affected by the region of silence must be identified. Based on assumption (i) above, the region of silence is much smaller than the non-silent brain region and some electrodes can be found on the scalp which are not substantially affected by the region of silence. These electrodes are discovered by calculating a power-ratio for each electrode (i.e., the power of electrode when there is a silent region, divided by the power of electrode when there is not any region of silent in the brain), as follows:

$$h^{(r)} = \left\{ [h_i] \middle| h_i = \frac{\left( \tilde{A} C_s^{(r-1)} \tilde{A}^T \right)_{ii}}{\left( \tilde{A} C_s^{full(r-1)} \tilde{A}^T \right)_{ii}} \right\}, \text{ for all } i = 1, 2, \ldots, n-1 \qquad (28)$$

where h is a vector with values 0 (all sources silent) and 1 (no silent source).

Using this power ratio, the electrodes are selected as follows:

$$S_{elec}^{(r)} = \{i | \text{indices of the } \phi \text{ maximum values in } h^{(r)}\} \qquad (29)$$

where:
$S_{elec}$ is the indices of the top φ electrodes which have the least power reduction due to the silent sources in $S$.

Based on the differential signals of the selected φ electrodes in Eq. (29), $\gamma^{(r)}$ and $\sigma_s^{(r)}$ are estimated as the least-square solutions in the following equation:

$$(\gamma^{(r)}, \sigma_s^{(r)}) = \underset{\gamma, \sigma_s}{\operatorname{argmin}} \sum \left\| \left( \tilde{A} C_s^{full}(\gamma, \sigma_s) \tilde{A}^T \right)_{ii} + \hat{\sigma}_{z_i}^2 - \widehat{Var}(y_{ii}) \right\|_2^2 \qquad (30)$$

(iii) Localization of Silent Sources in the High-Resolution Grid: Based on the correlatedness assumption of sources in the high-resolution grid, the source contribution measure definition from Eq. (13) is modified as follows:

$$\beta_q^{high(r)} := \frac{\text{Var}(\mu_{qt}) - \tilde{a}_q^T C_Z \tilde{a}_q}{\tilde{a}_q^T (\tilde{A} C_s^{full} \tilde{A}^T) \tilde{a}_q} \approx \frac{\widetilde{Var}(\mu_{qt}) - \tilde{a}_q^T \tilde{C}_r \tilde{a}_q}{\tilde{a}_q^T (\tilde{A} C_s^{full(r)} \tilde{A}^T) \tilde{a}_q} \quad (31)$$

where:

$\beta_q^{high(r)}$ takes values between 0 (all sources silent) and 1 (no silent sources).

The only difference between $\beta_q^{high(r)}$ in the high-resolution grid and $\beta_q$ in the low-resolution grid is in their denominators, which are essentially the variance terms in the absence of any silent source ($S^{max}(\mu_{qt})$ in Eq. (11)). In $\beta_q$, the denominator is divided by the source variance $\sigma_s^2$ to be able to calculate $\beta_q$ without estimation of $\sigma_s^2$. However, in the high-resolution grid, the denominator of $\beta_q^{high(r)}$ is simply $\widetilde{Var}^{max}(\mu_{qt})$, which is calculated under the source correlatedness assumption and using the estimated $C_s^{full(r)}$. Using the definition of source contribution measure $\beta_q^{high(r)}$ in the high-resolution grid, at iteration r, the contiguous region of silence is localized through a CSpeC framework, similar to the one defined in Eq. (14). However, the estimated source covariance matrix is used in each iteration to introduce a new set of constraints on the powers of the electrodes, which are less affected by the region of silence (i.e., the electrodes in $S_{elec}^{(r)}$ as defined in Eq. (29)). Based on these power constraints, a convex optimization framework to localize the region of silence in the high-resolution brain model is obtained as follows:

$$g^{*(r)}(\lambda, k, \zeta) = \beta^{high(r)T}(1-g) + \lambda(1-g)^T L(1-g), \quad (32)$$

$$s.t. g_i \in [0, 1], \text{ for all } i \in \{1, 2, \ldots, p\}$$

$$\|g\|_1 \leq p - k$$

$$\left(1^T (\tilde{A}_i C^{full(r)} \tilde{A}_i^T) g - \sigma_{z_i}^2 - \widetilde{Var}(y_i)\right)^2 \leq \zeta_i, \text{ for all } i \in S_{elec}^{(r)}$$

where:
$\beta^{high(r)T} = [\beta_1^{high(r)}, \ldots, \beta_p^{high(r)}]$;
$g = [g_1, \ldots, g_p]^T$;
$\zeta = [\zeta_1, \ldots, \zeta_\phi]^T$;
$\lambda$ and $\zeta_i$ are regularization parameters; and
$\tilde{A}_i$ is a diagonal matrix, with elements of the $i^{th}$ row of $\tilde{A}$ on its main diagonal, defined as:

$$\tilde{A}_i = \{\tilde{a}_{qv} | \tilde{a}_{qv}\}, \text{ for all } q = v, \tilde{a}_{qv} = 0 \text{ for all } q \neq v \quad (33)$$

In equation (32), $\zeta_i$ is chosen to be equal to the square of the residual error in Eq. (30), for each $i \in \Delta_{elec}$, i.e.:

$$\zeta_i = \left((\tilde{A} C_s^{full(r)}(\gamma^{(r)}, \sigma_S^{(r)}) \tilde{A}^T)_{ii} + \hat{\sigma}_{z_i}^2 - \widetilde{Var}(y_i)\right)^2 \quad (34)$$

In each iteration r, values of $\lambda$ and k are found in a similar way as to how they were found in the low-resolution grid (see Eqs. (21) and (22)). However, to estimate k based on Eq. (22), in the high-resolution grid, $C_s(k) = C_s^{(r)}$, is used as is defined in Eq. (26). After each iteration, the set of silent indices in $S^{(r)}$ is updated with the indices of the $\hat{k}$ smallest values in the solution of Eq. (32), i.e., $g^{*(r)}(\lambda, k, \zeta)$.

After convergence, i.e., when the convergence criterion is met (see Eq. (25)), the final estimate of region of silence is the set of source indices in $S^{r_{final}}$.

Choosing the best reference electrode: the final solution $S^{r_{final}}$ may change as different EEG reference electrodes are chosen, which changes the matrix of differential signals of scalp Y and the forward matrix A in Eq. (4). The question is how to choose a reference electrode which provides the best estimation of region of silence. To address this question, an approach similar to the estimation of $\hat{k}$, is used i.e., the reference electrode which gives us the minimum scalp power mismatch is chosen. The power mismatch $\Delta$Pow is defined as follows:

$$\Delta Pow = \sum_{i=1}^{n-1} \left\| \frac{(\tilde{A} C_s(\hat{k}) \tilde{A}^T)_{ii}}{\max_i (\tilde{A} C_s(\hat{k}) \tilde{A}^T)_{ii}} - \frac{\widetilde{Var}(y_i) - \hat{\sigma}_{z_i}^2}{\max_i \widetilde{Var}(y_i) - \hat{\sigma}_{z_i}^2} \right\|_2^2 \quad (35)$$

where both A and $y_i$ are calculated based on a specific reference electrode.

$\Delta$Pow is the total squared error between the normalized powers of scalp differential signals, resulting from the region of silence with size $\hat{k}$, and the estimated scalp powers based on the recorded data with a specific reference.

When baseline recordings are available—If a hemispheric baseline is considered, or, more generally, if a baseline recording is available, the 2-step algorithm remains largely the same. In an ideal case where a baseline recording of scalp potentials is available, the contribution of each source in the recorded scalp signals when there is a region of silence in the brain is compared with its contribution to the baseline recording. This results in a minor modification of the algorithm. The definitions of source contribution measures in Eqs. (14) and (31), should be changed as follows:

$$\tilde{\beta}_q = \min\left\{\frac{\beta_q}{\beta_q^{base}}, 1\right\}, \text{ for all } q \in \{1, 2, \ldots, p\} \quad (36)$$

where:
$\beta_q$ is defined in Eq. (13) for the low-resolution grid and in Eq. (31) for the high-resolution grid; and
$\beta_q^{base}$ is the corresponding contribution measure of source q in the baseline recording.

However, if the baseline recording is not available for the silence localization, based on the assumption of hemispheric symmetry, a hemispheric baseline can be used. The source contribution measure is defined in a relative way, i.e., each source's contribution measure is calculated in comparison with the corresponding source in the other hemisphere, as follows:

$$\tilde{\beta}_q = \begin{cases} \min\left\{\frac{\beta_q}{\beta_{q_m}}, 1\right\}, & \text{for all } q \in S^{LH} \cup S^{RH} \\ 1, & \text{for all } q \notin S^{LH} \cup S^{RH} \end{cases} \quad (37)$$

where
$S^{LH}$ is the set of indices of sources in the left hemisphere;
$S^{RH}$ is the set of indices of sources in the right hemisphere;
source indices which are not in $S^{LH} \cup \Delta^{RH}$ are located across the longitudinal fissure, which is defined as a strip of sources on the cortex, with a specific width $z^{gap}$; and $q_m$ in Eq. (37) is the index of the mirror source for source q, i.e., source q's corresponding source in the other hemisphere.

Eq. (37) reveals the advantage of having a baseline for the silence localization task, i.e., the identical distribution assumption of sources in the source contribution measure can be relaxed, which makes $\tilde{\beta}$robust against the violation of the identical distribution assumption of sources in the real world. The rest of the algorithm remains the same.

To find the solution of the CSpeC optimization in Eqs. (14) and (32), CVX, a MATLAB package for specifying and solving convex programs, is used. In addition, MATLAB nonlinear least-square solver is used to find the solution of Eq. (30).

Time complexity of the algorithm—The bottleneck of time complexity among the steps in the algorithm is the high-resolution convex optimization (see Eq. (32)). This is classified as a convex quadratically constrained quadratic program. However, the quadratic constraints in Eq. (32) are all scalar and each can be rewritten in forms of two linear constraints. This reduces the problem to a convex quadratic program, which can be solved either using semidefinite programming or second-order cone programming (SOCP).

However, it is much more efficient to solve the QPs using SOCP rather than using the general solutions for SDPs. The problem in equation (36) can be written as a SOCP with $v=2p+2\phi+1$ constraint of dimension one, and one constraint of dimension p+1, where p is the number of sources in the brain and $\phi$ is the number of selected electrodes in Eq. (29). Using the interior-point methods, the time complexity of each iteration is $\mathcal{O}(p^2(v+p+1)) \approx \mathcal{O}(p^3)$, where the number of iterations for the optimizer is upper bounded by $\mathcal{O}(\sqrt{v+1}) = \mathcal{O}(\sqrt{2p+2\phi+2})$ Therefore, the CSpeC framework for high resolution (see Eq. (32)) has the worst case time complexity of $\mathcal{O}(p^{3.5})$.

Similarly, the low-resolution CSpeC framework (see Eq. (14)), has the same time complexity of $\mathcal{O}(p^{3.5})$, since it only has $2\phi$ less linear constraints, in comparison with the quadratic program version of Eq. (32). It is important to mention that this time complexity is calculated without considering the sparsity of the graph Laplacian matrix (L) defined in Eq. (19). Exploiting such sparsity may reduce the computational complexity of solving the equivalent SOCP for the CSpeC framework. The other steps of the algorithm have lower degrees of polynomial time complexity (e.g., the least square solution in Eq. (30) with time complexity of $\mathcal{O}(2^2\phi)$, where $\phi \ll p$. Therefore, the general time complexity of the algorithm is $\mathcal{O}(\text{itr}_{ref}(p^{3.5}+\text{itr}_{conv} \cdot \text{itr}_k \cdot \text{itr}_\lambda(p^{3.5})) \approx \mathcal{O}(\text{itr}_{ref} \cdot \text{itr}_k \cdot \text{itr}_\lambda(p^{3.5}))$, including the number of iterations for finding the optimal regularization parameters (it $r_\lambda$ iterations for finding $\lambda^*$ in Eq. (21), and $\text{itr}_k$ iterations for finding $k^*$ in Eq. (22)), the required number of iterations for convergence of the algorithm to a region of silence in the high-resolution step ($\text{itr}_{conv}$), and the number of iterations to find the best reference electrode (it $r_{ref}$). It is worth mentioning that time required to run the algorithm depends on the resolution of the search grids for the parameters used in the algorithm, the resolution of the cortical models used, and the convergence criterion defined (see Eq. (25)).

The invention has been described in terms of specific implementations based on the use of specific tools. As would be realized by one of skill in the art, variations of the described methods and algorithms resulting in the desired outcome are possible and are considered to be within the scope of the invention, which is defined by the following claims.

The invention claimed is:

1. A method for localizing regions of silence in a brain comprising:
   localizing one or more contiguous regions of silence in a low-resolution grid of uncorrelated sources in the brain;
   using the one or more localized contiguous regions of silence in the low- resolution grid as an initial estimate of the location of the silence in a high-resolution grid of the sources in the brain; and
   iteratively localizing the one or more regions of silence in the high-resolution grid of correlated sources based on a covariance of the sources until a center-of-mass for each region of silence converges;
   wherein the contribution of each of the sources to the power component of the collected EEG signals is determined using a hemispheric baseline.

2. The method of claim 1 wherein the hemispheric baseline comprises:
   a ratio of a measured contribution in one hemisphere of the brain to a mirrored source from an opposite hemisphere of the brain.

3. The method of claim 2 wherein the mirrored sources are from a hemisphere of the brain having no regions of silence.

4. The method of claim 3 wherein the mirrored sources are measured with electrodes placed symmetrically with respect to a longitudinal fissure of the brain.

5. The method of claim 3 wherein readings from both hemispheres of the brain are recorded with respect to a reference electrode placed at a longitudinal fissure of the brain.

6. The method of claim 1 wherein the low-resolution grid is a coarse discretization of a cortex of the brain in which spatially-uncorrelated sources are localized.

7. The method of claim 1 wherein the high-resolution grid is a fine discretization of a cortex of the brain in which the sources are correlated.

8. The method of claim 1 wherein localizing the one or more contiguous regions of silence in the low-resolution grid further comprises:
   obtaining EEG readings of both hemispheres of the brain using a plurality of electrodes;
   determining, for each source, a cross-correlation coefficient indicating the contribution of the source to readings from each of the plurality of electrodes;
   calculating a normalized variance for each of the cross-correlation coefficients;
   deriving, based on the normalized variance, a source contribution measure for the low-resolution grid for each of the sources; and
   localizing silent sources in the low-resolution grid using convex spectral clustering based on the source contribution measures for the low-resolution grid.

9. The method of claim 8 wherein the cross-correlation coefficient is a ratio of the contribution of each uncorrelated source to a contribution of respective mirrored sources in the hemispheric baseline.

10. The method of claim 9 wherein a region of silence is indicated when the cross-correlation coefficient is close to zero.

11. The method of claim 1 wherein localizing the one or more regions of silence in the high-resolution grid further comprises:
    initializing a source variance variable, an exponential decay coefficient and a set containing a plurality of sources contributing to the one or more regions of silence;

performing an iteration of the following steps:
- determining a power ratio for each of the plurality of electrodes indicating a reduction in the power of the electrode due to the one or more regions of silence;
- determining a set of electrodes having a minimum reduction in power;
- based on the signals from the set of electrodes having a minimum power reduction, and values of the source variance variable and the exponential decay coefficient from a previous iteration, recalculating the source variance variable and the exponential decay coefficient;
- calculating a source covariance matrix based on the source variance variable and the exponential decay coefficient;
- calculating a source contribution measure for the high-resolution grid for each of the sources based on the covariance matrix;
- localizing silent sources in the high-resolution grid using convex spectral clustering based on the source contribution measures for the high-resolution grid; and
- updating the set of silence sources.

12. The method of claim 1 further comprising:
estimating a size of the one or more regions of silence.

13. The method of claim 1 wherein the iteration continues for a pre-determined number of iterations.

14. The method of claim 1 further comprising:
calculating a source contribution measure for the low-resolution grid and the high-resolution grid by comparison of respective source contribution measures to the source contribution measure for the respective mirrored source in the hemispheric baseline.

* * * * *